(12) United States Patent
Wu

(10) Patent No.: US 8,745,842 B2
(45) Date of Patent: Jun. 10, 2014

(54) METHOD FOR ATTACHING RADIOPAQUE MARKERS TO A STENT

(75) Inventor: Patrick P. Wu, Mountain View, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 69 days.

(21) Appl. No.: 13/399,896

(22) Filed: Feb. 17, 2012

(65) Prior Publication Data

US 2012/0151744 A1 Jun. 21, 2012

Related U.S. Application Data

(62) Division of application No. 12/881,968, filed on Sep. 14, 2010, now Pat. No. 8,127,422, which is a division of application No. 11/771,974, filed on Jun. 29, 2007, now abandoned.

(60) Provisional application No. 60/830,201, filed on Jul. 11, 2006.

(51) Int. Cl.
*A61F 2/06* (2013.01)

(52) U.S. Cl.
USPC .............................................. 29/505; 29/525

(58) Field of Classification Search
USPC .................... 29/505, 525, 508, 516, 517, 529
See application file for complete search history.

(56) References Cited

U.S. PATENT DOCUMENTS

| | | | |
|---|---|---|---|
| 3,068,563 A | 12/1962 | Reverman | |
| 4,361,948 A * | 12/1982 | Omata | 29/517 |
| 6,022,374 A | 2/2000 | Imran | |
| 6,334,871 B1 | 1/2002 | Dor et al. | |
| 6,464,720 B2 | 10/2002 | Boatman et al. | |
| 6,506,437 B1 | 1/2003 | Harish et al. | |
| 6,673,106 B2 | 1/2004 | Mitelberg et al. | |
| 6,726,713 B2 | 4/2004 | Schaldach et al. | |
| 6,769,161 B2 | 8/2004 | Brown et al. | |
| 6,918,928 B2 | 7/2005 | Wolinsky et al. | |
| 6,926,733 B2 | 8/2005 | Stinson | |
| 2003/0069630 A1 | 4/2003 | Burgermeister et al. | |
| 2004/0088039 A1 | 5/2004 | Lee et al. | |
| 2004/0181236 A1 | 9/2004 | Eidenschink et al. | |
| 2004/0204750 A1 | 10/2004 | Dinh | |
| 2005/0004653 A1 | 1/2005 | Gerberding et al. | |
| 2005/0015138 A1 | 1/2005 | Schuessler et al. | |
| 2005/0154450 A1 | 7/2005 | Larson et al. | |
| 2005/0283228 A1 | 12/2005 | Stanford | |

* cited by examiner

*Primary Examiner* — David Bryant
*Assistant Examiner* — Christopher Besler
(74) *Attorney, Agent, or Firm* — Squire Sanders (US) LLP

(57) ABSTRACT

A mandrel for supporting a stent and rollers for pressing a radiopaque marker into a stent are disclosed. The mandrel can have a forward portion for carrying the stent and a rear portion for urging the stent forward portion into a gap between the rollers. The mandrel may be pushed or pulled into the gap, which is sized to allow the rollers to press the marker into engagement with the stent. Prior to moving the mandrel into the gap, the marker may be placed on a surface of the stent or partially inside a recess in the stent. Several markers can be efficiently and uniformly pressed onto the stent by moving the mandrel into the gap in one continuous movement in an axial or lateral direction. Markers can also be pressed onto the stent by placing the stent in the gap and rotating the stent about its central axis.

19 Claims, 5 Drawing Sheets

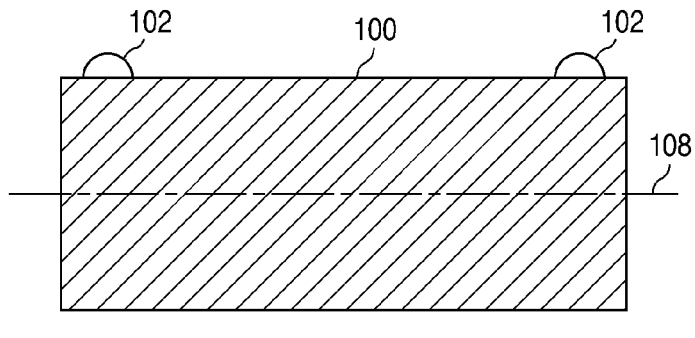
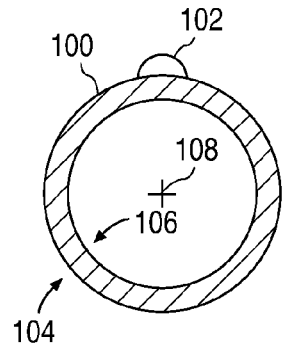
FIG. 5  FIG. 6
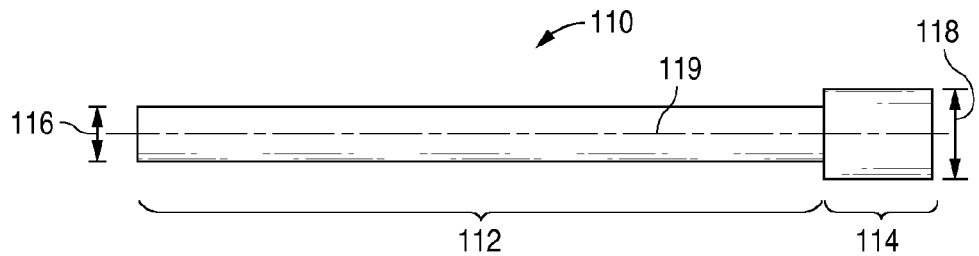
FIG. 7
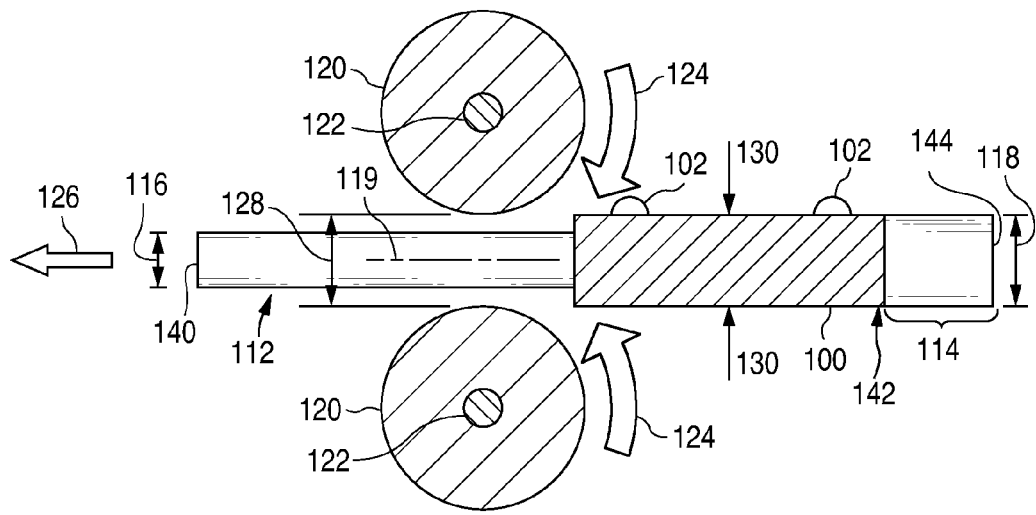
FIG. 8

METHOD FOR ATTACHING RADIOPAQUE MARKERS TO A STENT

This application is a divisional application of U.S. application Ser. No. 12/881,968 filed on Sep. 14, 2010, which is a divisional application of U.S. application Ser. No. 11/771,974 filed on Jun. 29, 2007, now abandoned, which claims the benefit of U.S. Provisional Application No. 60/830,201 filed on Jul. 7, 2006. The entire contents of each of the above applications are incorporated herein by reference.

BACKGROUND OF THE INVENTION

1. Field of the Invention

This invention relates generally to implantable medical devices, such as stents, and, more particularly, to attaching radiopaque markers to polymeric stents.

2. Description of the State of the Art

Expandable endoprostheses are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce blood vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The structure of stents is typically composed of scaffolding that includes a pattern or network of interconnecting structural elements or struts. The scaffolding can be formed from wires, tubes, or sheets of material rolled into a cylindrical shape. In addition, a medicated stent may be fabricated by coating the surface of either a metallic or polymeric scaffolding with a polymeric carrier. The polymeric scaffolding may also serve as a carrier of an active agent or drug.

The first step in treatment of a diseased site with a stent is locating a region that may require treatment such as a suspected lesion in a vessel, typically by obtaining an x-ray image of the vessel. To obtain an image, a contrast agent, which contains a radiopaque substance such as iodine is injected into a vessel. "Radiopaque" refers to the ability of a substance to absorb x-rays. The x-ray image depicts the lumen of the vessel from which a physician can identify a potential treatment region. The treatment then involves both delivery and deployment of the stent. "Delivery" refers to introducing and transporting the stent through a bodily lumen to a region in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn allowing the stent to self-expand.

The stent must be able to simultaneously satisfy a number of mechanical requirements. First, the stent must be capable of withstanding the structural loads, namely radial compressive forces, imposed on the stent as it supports the walls of a vessel lumen. In addition to having adequate radial strength or more accurately, hoop strength, the stent should be longitudinally flexible to allow it to be maneuvered through a tortuous vascular path and to enable it to conform to a deployment site that may not be linear or may be subject to flexure. The material from which the stent is constructed must allow the stent to undergo expansion, which typically requires substantial deformation of localized portions of the stent structure. Once expanded, the stent must maintain its size and shape throughout its service life despite the various forces that may come to bear thereon, including the cyclic loading induced by the beating heart. Finally, the stent must be biocompatible so as not to trigger any adverse vascular responses.

In addition to meeting the mechanical requirements described above, it is desirable for a stent to be radiopaque, or fluoroscopically visible under x-rays. Accurate stent placement is facilitated by real time visualization of the delivery of a stent. A cardiologist or interventional radiologist can track the delivery catheter through the patient's vasculature and precisely place the stent at the site of a lesion. This is typically accomplished by fluoroscopy or similar x-ray visualization procedures. For a stent to be fluoroscopically visible it must be more absorptive of x-rays than the surrounding tissue. Radiopaque materials in a stent may allow for its direct visualization.

In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials may be configured to meet this additional clinical requirement since they may be designed to completely erode after the clinical need for them has ended. Stents fabricated from biodegradable polymers are particularly promising, in part because they may be designed to completely erode within a desired time frame.

However, a significant shortcoming of biodegradable polymers (and polymers generally composed of carbon, hydrogen, oxygen, and nitrogen) is that they are radiolucent with no radiopacity. Biodegradable polymers tend to have x-ray absorption similar to body tissue.

One way of addressing this problem is to attach radiopaque markers to structural elements of the stent. A radiopaque marker can be disposed within a structural element in such a way that the marker is secured to the structural element. However, the use of stent markers on polymeric stents entails a number of challenges. One challenge relates to the difficulty of insertion of markers.

Another challenge pertains to the fact that some regions of polymeric struts tend to undergo significant deformation or strain during crimping and expansion. In particular, such changes are due to plastic deformation of polymers. Thus, during stent deployment, the portion of a stent containing an element may crack or stretch as stress is being applied to the expanding stent. As a result, the marker may become dislodged.

Attachment of radiopaque markers to stents usually requires a significant amount of time to perform with reliability and uniformity. The amount of time required is increased when several markers must be attached at different locations on the stent. Also, conventionally-placed markers may project inward from the luminal surface of the stent to such a degree that blood flow is disrupted, or project outward from the abluminal surface of the stent to such a degree that the walls of the blood vessel are traumatized.

Accordingly there is a need to for an apparatus and method of easily attaching radiopaque markers on stents. There is also a need for an apparatus and method of attaching radiopaque markers on stents such that the marker is retained in the stent during deformation of the stents during subsequent stent crimping and expansion. There is a further need for an apparatus and method of attaching a plurality of radiopaque markers to a stent with greater efficiency and uniformity. Also, there is a need to attach radiopaque markers such that the radiopaque markers do not overly protrude from the stent. The present invention satisfies these and other needs.

SUMMARY OF THE INVENTION

Various embodiments of the present invention include a method of attaching a radiopaque marker onto a stent, the method comprising: placing a stent mounted on a mandrel into a gap between a first roller and a second roller, the stent including a radiopaque marker positioned at a surface of the stent, wherein both of the rollers are oriented such that their rotational axes are substantially parallel to the central axis of the stent; wherein the rollers rotate in the same direction, wherein the stent is rotated about its central axis in a direction opposite to the rollers thereby bringing the markers into contact with the first or second roller; and allowing the first or second roller to press the radiopaque marker in a manner that couples the radiopaque marker to the stent.

Further embodiments of the present invention include a method of attaching a radiopaque marker onto a stent, the method comprising: placing a stent mounted on a mandrel into a gap between a first roller and a second roller, the stent including a radiopaque marker positioned at a surface of the stent, wherein both of the rollers are oriented such that their rotational axes are substantially parallel to the central axis of the stent, wherein the rollers are rotated about the central axis of the stent thereby bringing the rollers into contact with the markers, wherein the stent is rotated about its central axis in a direction opposite to the rollers; and as the rollers continue to rotate, allowing the rollers to press the radiopaque marker in a manner that couples the radiopaque marker to the stent.

The features and advantages of the invention will be more readily understood from the following detailed description which should be read in conjunction with the accompanying drawings.

BRIEF DESCRIPTION OF THE DRAWINGS

FIG. 5 is a side view showing a stent with two radiopaque markers disposed over openings in the stent.

FIG. 6 is an end view showing the stent and one of the markers of FIG. 5.

FIG. 7 is a side view showing a mandrel for carrying a stent, the mandrel having a forward portion and a rear portion.

FIG. 8 is a side view of an apparatus for attaching radiopaque markers onto a stent, showing the mandrel of FIG. 7 carrying the stent of FIG. 5, and showing rollers having a rotational axis substantially perpendicular to the central axis of the stent, and the forward portion of the mandrel placed in a gap between the rollers.

DETAILED DESCRIPTION OF THE INVENTION

The present invention may be applied to stents and, more generally, implantable medical devices such as, but is not limited to, self-expandable stents, balloon-expandable stents, stent-grafts, vascular grafts, cerebrospinal fluid shunts, pacemaker leads, closure devices for patent foramen ovale, and synthetic heart valves.

A stent can have virtually any structural pattern that is compatible with a bodily lumen in which it is implanted. Typically, a stent is composed of a pattern or network of circumferential and longitudinally extending interconnecting structural elements or struts. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility. The present invention is applicable to virtually any stent design and is, therefore, not limited to any particular stent design or pattern. One embodiment of a stent pattern may include cylindrical rings composed of struts. The cylindrical rings may be connected by connecting struts.

A stent may be formed from a tube by laser cutting the pattern of struts in the tube. The stent may also be formed by laser cutting a polymeric sheet, rolling the pattern into the shape of the cylindrical stent, and providing a longitudinal weld to form the stent. Other methods of forming stents are well known and include chemically etching a polymeric sheet and rolling and then welding it to form the stent. A polymeric wire may also be coiled to form the stent. The stent may be formed by injection molding of a thermoplastic or reaction injection molding of a thermoset polymeric material. Filaments of the compounded polymer may be extruded or melt spun. These filaments can then be cut, formed into ring elements, welded closed, corrugated to form crowns, and then the crowns welded together by heat or solvent to form the stent. Lastly, hoops or rings may be cut from tubing stock, the tube elements stamped to form crowns, and the crowns connected by welding or laser fusion to form the stent.

Figure 1:
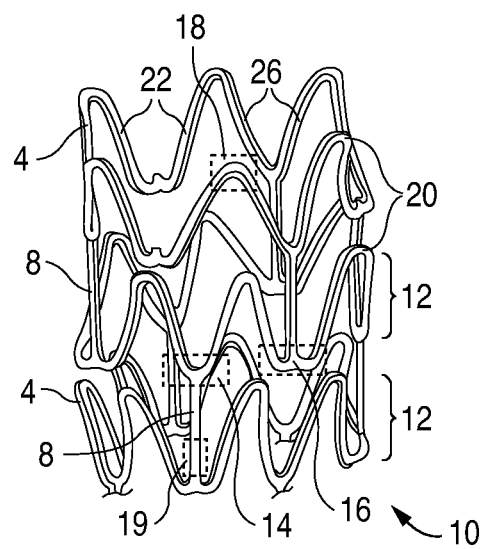
FIG. 1 is a perspective view showing a cylindrically-shaped stent.

Referring now in more detail to the exemplary drawings for purposes of illustrating embodiments of the invention, wherein like reference numerals designate corresponding or like elements among the several views, there is shown in FIG. 1 a cylindrically-shaped stent 10 with struts 4 that form cylindrical rings 12 which are connected by linking struts 8. The cross-section of the struts in stent 10 is rectangular-shaped. The struts have abluminal faces 20, luminal faces 22, and sidewall faces 26. The cross-section of struts is not limited to what has been illustrated, and therefore, other cross-sectional shapes are applicable with embodiments of the present invention. The pattern should not be limited to what has been illustrated as other stent patterns are easily applicable with embodiments of the present invention.

A stent can be made of a biostable and/or biodegradable polymer. As indicated above, a stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain.

It is generally desirable to minimize the interference of a stent or marker with the structure of a lumen and/or with flow of bodily fluid through the lumen. Sharp edges, protrusions, etc. in the path of blood flow can result in formation of turbulent and stagnant zones which can act as a nidus for thrombosis. A smaller and/or smoother profile of a body portion may be more hemocompatible. Additionally, a smaller and smoother profile presented by a marker has much less likelihood of catching on other parts of the delivery system such as the guidewire or guiding catheter. The embodiments discussed herein involve markers, which after having been pressed into engagement onto a stent, do not contribute significantly to the form factor, or profile, of the stent in such a way that interferes with the structure of a lumen and/or with flow of bodily fluid through the lumen.

As indicated above, it is desirable to have the capability of obtaining images of polymeric stents with x-ray fluoroscopy during and after implantation. Various embodiments of the present invention involve stents with markers disposed within depots or holes in a stent. A depot may be formed in a structural element by laser machining The depot may extend partially or completely through the portion of the stent. For example, an opening of a depot may be on an abluminal or luminal surface and extend partially through the stent or completely through to an opposing surface. The markers may be sufficiently radiopaque for imaging the stent.

Figure 2:
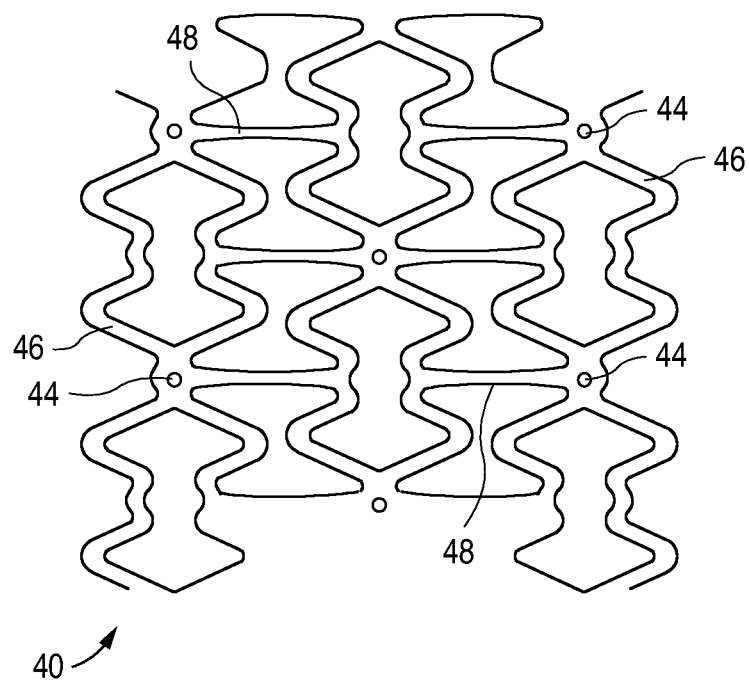
FIG. 2 is a plan view showing a flattened stent pattern with depots for receiving radiopaque markers.

FIG. 2 shows a stent pattern 40 with depots 44 for receiving a marker. In FIG. 2, the stent pattern 40 is shown in a flattened condition showing an abluminal or luminal surface so that the pattern can be clearly viewed. When the flattened portion of the stent pattern 40 is in a cylindrical condition, it forms a radially expandable stent. The stent pattern 40 includes cylindrically aligned structural elements 46 and linking structural elements 48.

Figure 3:
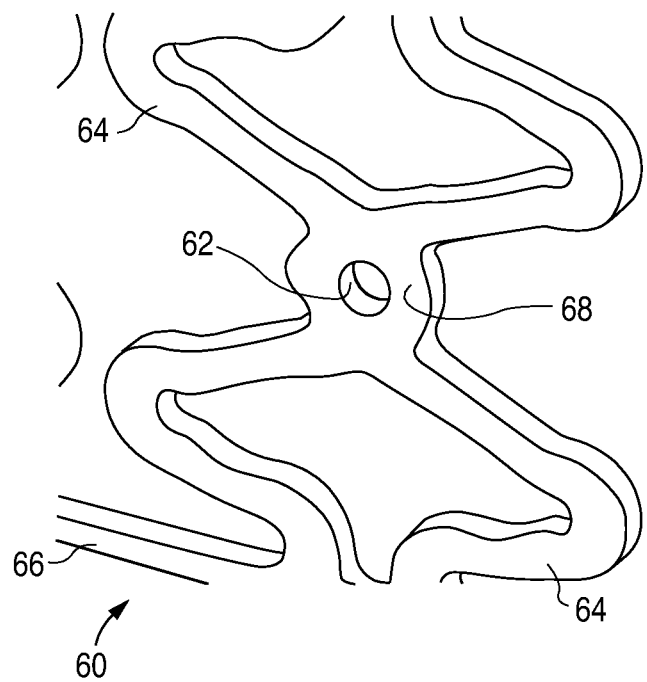
FIG. 3 is a perspective view of a portion of a stent, showing a depot for receiving a radiopaque marker.

FIG. 3 shows a portion of a stent 60 with a depot 62 for retaining a radiopaque marker. The stent 60 includes cylindrically aligned structural elements 64 and linking structural elements 66. The depot 62 is located in a portion 68 which is a region of intersection of four structural elements. As depicted in FIG. 3, the depot 62 has a cylindrical shape and extends completely through the radial thickness of the structural elements 64.

Certain embodiments of the present invention involve a deformed radiopaque marker disposed in a depot in a portion of the stent. The marker may be coupled to the portion at least partially by an interference or press fit between an expanded section of the marker and an internal surface of the portion of the stent within the depot. In some embodiments, a marker in an undeformed state may be disposed in a depot and compressed to couple the marker within the depot. Compressing the marker may expand a portion of the marker within the depot to create the interference fit. Alternatively, the stent material may deform to achieve the interference fit with little or no deformation of the marker.

Figure 4:
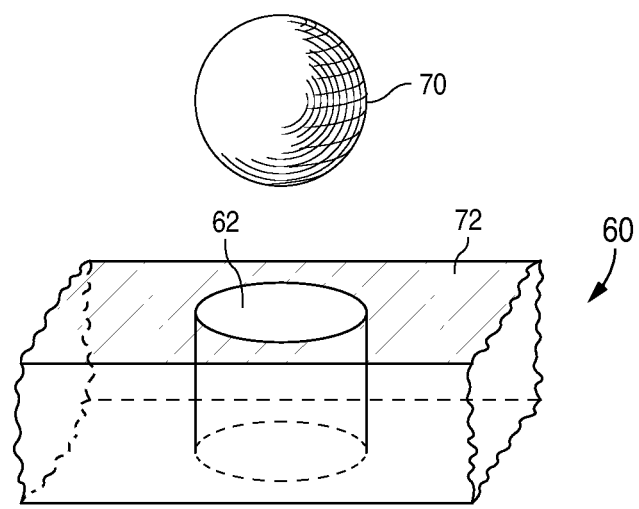
FIG. 4 is a perspective view of the stent of FIG. 3, showing a spherical radiopaque marker disposed over the depot.

FIG. 4 shows a marker 70 disposed over the depot 62 extending through an abluminal surface 72 of the stent 60. In practice, the marker 70 may be positioned using a syringe so that the marker rests on top of the abluminal surface 72, partially inside the depot 62, or both. The marker 70 may be held at the end of the syringe by a vacuum or surface tension of a viscous fluid.

The present invention encompasses markers fabricated by methods including, but not limited to, molding, machining, assembly, or a combination thereof. All or part of a metallic or polymeric marker may be fabricated in a mold or machined by a method such as laser machining. Markers can have any shape or size. Preferably, though not necessarily, the markers are spherical in shape. Compared to markers of a cylindrical or other shape having a longitudinal axis, spherical markers are easier to align for placement on top of or into an opening formed in the stent.

Markers may be biodegradable. It may be desirable for the markers to degrade at the same or substantially the same rate as the stent. For instance, the markers may be configured to completely or almost completely erode at the same time or approximately the same time as the stent. Alternatively, the markers may degrade at a faster rate than the stent. In this case, the markers may completely or almost completely erode before the body of the stent is completely eroded.

Also, a biocompatible biodegradable metal may be used for the markers. A biocompatible biodegradable metal forms erosion products that do not negatively impact bodily functions. The markers may be composed of a pure or substantially pure biodegradable metal. Representative examples of biodegradable metals for use in a marker may include, but are not limited to, magnesium, zinc, and iron. Representative mixtures or alloys may include magnesium/zinc, magnesium/iron, zinc/iron, and magnesium/zinc/iron. Radiopaque compounds such as iodine salts, bismuth salts, or barium salts may be compounded into the metallic biodegradable marker to further enhance the radiopacity. Other representative examples of biostable metals include platinum and gold.

Further, the markers may be a mixture of a biodegradable polymer and a radiopaque material. The radiopaque material may be biodegradable and/or bioabsorbable. Representative radiopaque materials may include, but are not limited to, biodegradable metallic particles and particles of biodegradable metallic compounds such as biodegradable metallic oxides, biocompatible metallic salts, gadolinium salts, and iodinated contrast agents.

Certain embodiments of the present invention include disposing, coupling, or pressing radiopaque markers within a recess or depot in a stent structure. Such embodiments are described below in connection with FIGS. 7-12.

FIGS. 5 and 6 show a stent 100 with markers 102 protruding radially from the stent 100. The markers 100 have been placed partially inside recesses formed in the stent. The recesses are not shown for clarity and ease of illustration. The recesses can be depots that extend completely through a stent structure, from an abluminal surface 104 to a luminal surface 106. Alternatively, the recesses can be cavities that extend partially into the stent structure. The terms "recess" and "opening" are used interchangeably herein. The stent has a central axis 108 extending along the entire length of the stent 100.

FIG. 7 shows a step mandrel 110 having a forward portion 112 and a rear portion 114. The forward portion 112 has a diameter 116 that is less than the diameter 118 of the rear portion 114. The forward portion is adapted to carry the stent 100. The mandrel 110 has a longitudinal axis 119 extending along the entire length of the mandrel. The mandrel 110 can be made of a relatively rigid material, in comprarison to a stent, selected to provide firm support for the stent. Examples of suitable materials includes plastics, such as Delrin, PVC, nylon, and others; metals such as steel, stainless steel, aluminum, titanium, and others; and glass. The mandrel 110 can also include a relatively resilient and compliant material that is selected to provide sufficient support to the stent and to cushion the stent from excessive pressure from rollers described below.

In FIG. 8, the stent 100 has been mounted onto the forward portion 112 of the mandrel 110, which has been moved between two rollers 120 that may rotate about a retaining pin 122 in the direction of rotational arrows 124. The forward portion 112 supports the stent 100 at its luminal surface when the markers 102 are later pressed onto the stent. The rollers 120 have a circular cross-section. The retaining pin 122 is substantially perpendicular to the central axis of the stent, which allows each roller 120 to rotate about an axis that is substantially perpendicular to the longitudinal axis 119 of the stent 100. Further movement of the mandrel 110 and the stent 100 in the direction of axial arrow 126 will cause the markers 102 to be pressed into the surface of the stent 100 without damaging stent 100.

The rollers 120 can be made of a relatively rigid material, in comparison to the stent 100 and markers 102, to facilitate pressing the markers into engagement with stent. Examples of suitable materials includes plastics, such as Delrin, PVC, nylon, and others; metals such as steel, stainless steel, aluminum, titanium, and others; and glass. The rollers 120 can also include a relatively resilient and compliant material that is selected to avoid damaging the stent 100 or markers 102 yet provide sufficient pressure to press the markers into engagement with the stent.

In some embodiments, the rollers 120 are positioned over the mandrel 110 such that the top roller 120 does not contact stent 100 and contacts only the markers 102. In this way, stress on the stent 100 is minimized. The bottom roller 120 contacts the stent to support the stent when the top roller 120 presses the markers 120. The markers 102 are compacted tightly against the opening of stent 100 and the markers 102 are retained in the stent during stent crimping, delivery, and deployment in a bodily lumen.

Figure 9:
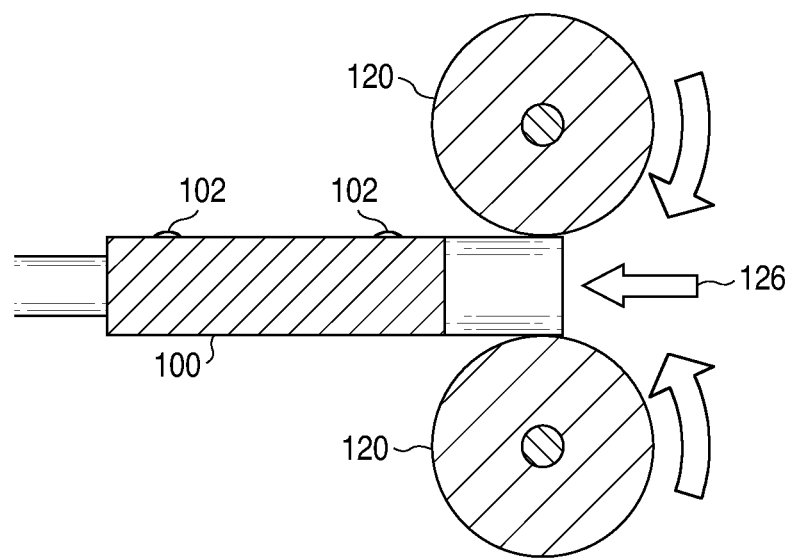
FIG. 9 is a side view of the apparatus of FIG. 8 showing the mandrel and stent having been moved axially through the gap between the rollers and showing the markers pressed into engagement with the stent.

FIG. 9 shows the stent 100 and mandrel 110 after having been moved axially in the direction of axial arrow 126 from their positions in FIG. 8. As a result, the markers 102 have been pressed into the openings of stent 100 to fabricate a stent with markers that partially protrude from the stent 100. In one embodiment, the rollers 120 cause the markers 102 to deform to reduce or eliminate protrusion of the markers 102 from the stent 100. Thus, the invention provides a method and apparatus for pressing markers into the stent such that the marker is tightly fit into the stent, thereby improving marker retention onto the stent as well as reducing or eliminating protrusion of the marker from the stent.

Figure 10:
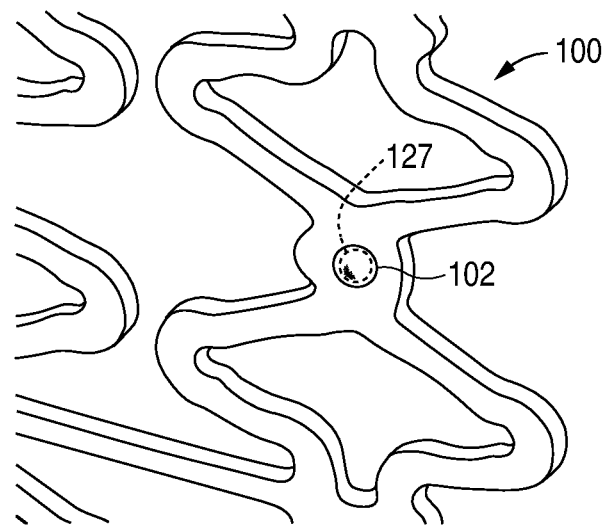
FIG. 10 is a perspective view of a portion of the stent of FIG. 5, showing one of the radiopaque markers pressed into engagement with the stent after having passed through the gap between the rollers.

Both markers 102 have been pressed into engagement with the stent 100 with one continuous axial movement of the mandrel 110 carrying the stent 100. FIG. 10 shows one of the markers 102 after having been pressed into one of the openings 127 of the stent 100. Although only two markers 102 are illustrated in FIGS. 8 and 9, it will be appreciated that any number of markers may be positioned on the stent and pressed into engagement with efficiency by one continuous axial movement of the mandrel 110. Use of the same set of rollers 120 on all the markers allows for uniformity in pressing the markers into engagement with the stent 100.

In other embodiments, the stent 100 may be passed through the gap 128 between the rollers 120 in a plurality of discrete movements. In yet other embodiments, the stent 100 may be passed through the gap 128 more than one time in order to press markers located at other portions of the stent. Also, the stent 100 may be passed through the gap 128 more than one time to press the markers into engagement with the stent 100 in a progressive fashion. For example, the gap 128 may be decreased after each time the stent 100 passes through the gap.

Referring again to FIG. 8, the gap 128 between the two rollers may be equal to or slightly larger than the outer diameter 130 of stent 100, thereby avoiding damage to the stent. The outer diameter 118 of the rear portion 114 of the mandrel 110 may be made equal to or substantially equal to the stent outer diameter 130. The outer diameter 118 may be greater than or equal to the stent outer diameter 130. Also, the outer diameter 116 of the mandrel forward portion 112 may be equal to or smaller than the inner diameter of the stent 100. In this way, the stent 100 can have a slip or interference fit with the mandrel forward portion 112.

The markers 102 are deformed by pushing the stent 100 through the rollers 120. When the stent 100, having luminal surfaces supported by the forward portion 112 of the mandrel 110, is pushed through the rollers 120, the markers 102 are pressed inward and against the stent by the rollers 120.

In practice, the free end 140 of the mandrel forward portion 112 may be pulled axially in the direction of axial arrow 126 until the markers 102 are pressed by the rollers 120. In this manner, the mandrel rear portion 114 engages a rear end 142 of the stent 100 so as to push the stent 100 into the gap 128 between the rollers.

In some embodiments, the free end 144 of the mandrel rear portion 114 may be pushed axially in the direction of axial arrow 126 until the markers 102 are pressed by the rollers 120.

FIGS. 8 and 9 show how the stent 100 can be linearly translated relative to the rollers 120. Linear translation of the stent 100 relative to the rollers 120 can be achieved in other ways. For example, in other embodiments, the stent 100 and the mandrel 110 are held fixed in position while the rollers 120 are moved axially over the stent and mandrel until the markers 102 are pressed into engagement with the stent. In yet other embodiments, the mandrel 110 and rollers 120 are both moved relative to each other to facilitate pressing the markers 102 onto the stent 100.

It will be appreciated that any number of rollers may be used. For example, the mandrel 110 may be supported at one or both its ends such that the bottom roller 102 in FIGS. 8 and 9 can be eliminated, and only the top roller 120 in FIGS. 8 and 9 is needed to press the markers 102 into engagement with the stent 100. More than two rollers, on the same or different sides of the stent 100, may be used to provide greater support of the stent 100 or to guide the mandrel 110 into the gap between the rollers. Also, more than two rollers may be used to press markers in a progressive fashion. For example, a first set of rollers may be used to press the markers onto the stent, and a second set of rollers that are spaced closer together may be used to press the markers further onto the stent. Progressive sets of rollers can have gaps between them that become smaller with each succeeding set of rollers.

Figure 11:
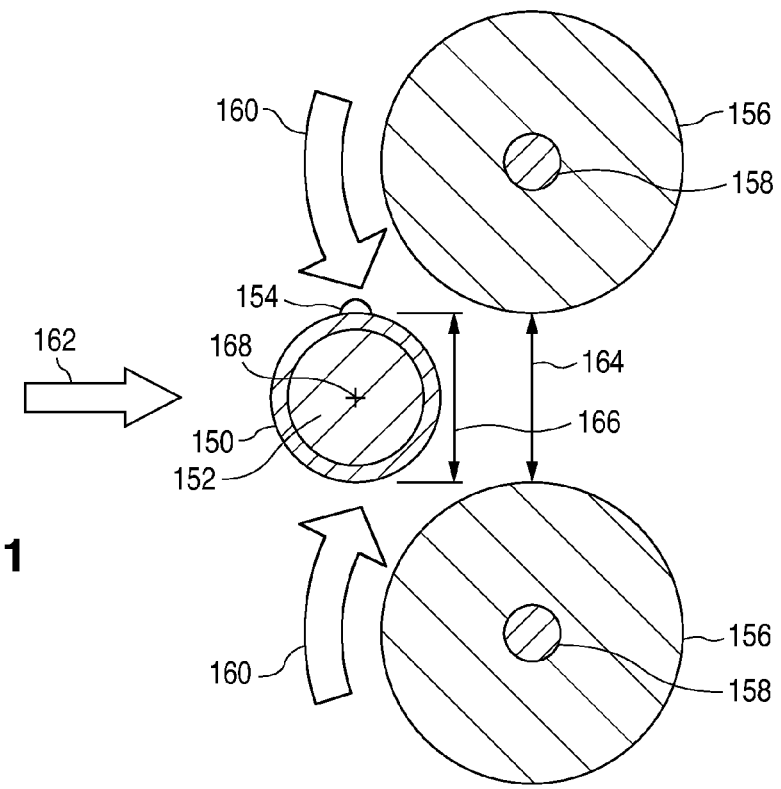
FIG. 11 is a side view of a marker attachment apparatus, showing a stent mounted on a mandrel and rollers adjacent the stent and mandrel, the rollers having a rotational axis substantially parallel to the central axis of the stent such that a marker and the stent are pressed into engagement with each other when the stent is moved laterally through a gap between the rollers.

FIG. 11 shows an apparatus and method in accordance with another embodiment of the present invention. A stent 150 is mounted over a mandrel 152. A radiopaque marker 154 has been placed on the stent 150. Two rollers 156, adjacent the stent 150, are vertically aligned and are oriented such that a retaining pin 158 at the center of each roller is substantially parallel to the central axis of the stent 150. In this way, each of the rollers 156 may rotate along the direction of rotational arrows 160 about a rotational axis that is substantially parallel to the central axis of the stent.

Instead of being moved axially as in FIG. 9, the stent 150 and the mandrel 152 of FIG. 11 are moved laterally along the direction of lateral arrow 162 into a gap 164 between the rollers 156. The stent 150 is oriented such that the marker 154 is pressed into engagement against the stent as the stent passes through the gap 164. The lateral direction of movement of the stent 150 is substantially perpendicular to the central axis of the stent 150. In other embodiments, the lateral direction is at an angle between zero and ninety degrees from the central axis of the stent 150.

Preferably, the stent 150 is prevented from rotating about its central axis 168 while the stent passes through the gap 164. For example, the stent 150 may be held on the mandrel 152 with a slight interference fit, and the ends of the mandrel 152 may be secured against rotation. Also, the top roller 156 preferably rotates along the direction of arrow 160 while the marker 154 passes beneath it to ensure that the marker is pressed downward onto the stent 150 and to avoid pushing the marker sideways.

Referring again to FIG. 11, the gap 164 is carefully selected to allow the stent 150 to pass through the gap 164 without being damaged. Preferably, the vertical size of the gap 164 is greater than or equal to the outer diameter 166 of the stent 150. The vertical size of the gap 164 is selected such that the rollers provide sufficient pressure to deform the marker 154 into engagement with an opening in the stent 154 and to reduce the amount with which the marker 154 protrudes radially from the stent 154.

Figure 12:
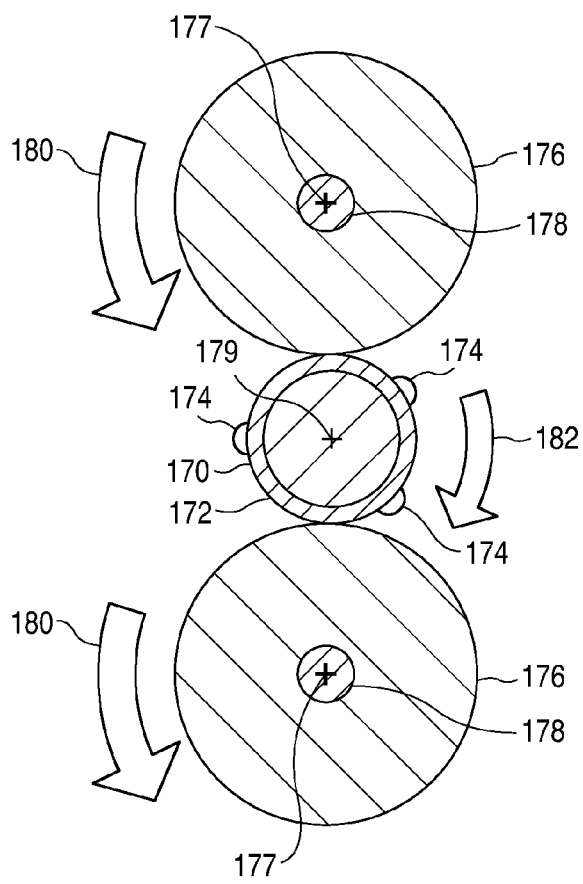
FIG. 12 is a side view of a marker attachment apparatus, showing a stent mounted on a mandrel and rollers adjacent the stent and mandrel, the rollers having a rotational axis substantially parallel to the central axis of the stent such that a marker and the stent are pressed into engagement with each other when the stent is placed between a gap between the rollers and rotated about its central axis.

FIG. 12 shows an apparatus and method in accordance with yet another embodiment of the present invention. A stent 170 is mounted over a mandrel 172. Three radiopaque makers 174 have been placed on the stent 170. Two rollers 176, adjacent the stent 170, are each held by a retaining pin 178. The rollers 176 are vertically aligned and are oriented such that their rotational axes 177 are substantially parallel to the central axis 179 of the stent 170. In this way, the rollers 176 may rotate along the direction of rotational arrows 180. The stent 170 is placed between in the gap between the two rollers 176. The stent 170 is oriented such that the markers 174 avoid contact with the rollers when first placed in the gap. Then, the stent 170 is rotated about its central axis along rotational arrow 182, thereby bringing the markers 174 into contact with the rollers. As the stent 170 continues to rotate, the rollers 176 press the markers 174 into engagement with the stent.

FIG. 12 shows how the stent 170 can be rotationally translated relative to the rollers 176. Rotational translation of the stent 170 relative to the rollers 176 can be achieved in other ways. For example, in other embodiments, the rollers 176 may rotate about the central axis 179 of the stent 170. After the stent 170 is placed between in the gap between the two rollers 176, the rollers 176 are rotated about the central axis 179 of the stent 170 while the stent 170 is prevented from rotating about its central axis 179, thereby bringing the rollers 176 into contact with the markers 174. As the rollers 176 continue to rotate, the rollers 176 press the markers 174 into engagement with the stent 170. Further, in other embodiments, both the stent 170 and the rollers 176 are rotated about the central axis 179 of the stent 170.

Although three markers 174 are illustrated in FIG. 12, it will be appreciated that any number of markers may be positioned on the stent and pressed into engagement with efficiency by one continuous rotational movement of the stent 170. It will also be appreciated that additional rollers may be used. Additional rollers may be used to provide greater support to the stent 170 or help keep the stent aligned within the gap between the rollers.

In FIGS. 8-12, the retaining pins at the center of the rollers are fixed in position relative to each other. In other embodiments, retaining pins are movable relative to each other. For example, movable retaining pins may be held by a spring or device the biases the rollers to achieve a nominal gap between the rollers. The nominal gap may be less than, equal to, or greater than the outer diameter of the stent. When the stent is passed through the gap, the spring or other biasing device allows the rollers to move apart so as to maintain a selected level of pressure on the stent and marker. In this manner, the risk of damage to the stent and marker is reduced.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A method of attaching a radiopaque marker onto a stent, the method comprising:
    placing a stent mounted on a mandrel into a gap between a first roller and a second roller, the stent including a radiopaque marker positioned over a recess formed in a strut of the stent, the gap in which the stent is placed is sized to allow the stent to pass between the first and second rollers,
    wherein both of the rollers are rotated and oriented such that rotational axes of the rollers arc substantially parallel to a central axis of the stent; and
    allowing the first or second roller to press the radiopaque marker into the recess formed in the strut of the stent while the stent is in the gap.

2. The method of claim 1, wherein the stent is supported by the mandrel while the radiopaque marker is pressed with the first or second roller.

3. The method of claim 1, wherein each roller rotates about a retaining pin at a center of each roller.

4. The method of claim 1, wherein the radiopaque marker is deformed when it is pressed into the recess to reduce or eliminate protrusion of the radiopaque marker from the stent.

5. The method of claim 1, wherein the size of the gap is selected such that the rollers provide sufficient pressure to deform the radiopaque marker into engagement with the recess.

6. The method of claim 1, wherein the stent is oriented such that the radiopaque marker avoids contact with the rollers when the stent is first placed in the gap.

7. A method of attaching a radiopaque marker onto a stent, the method comprising:

placing a stent mounted on a mandrel into a gap between a first roller and a second roller, the stent including a radiopaque marker positioned at a surface of the stent, wherein both of the rollers are oriented such that rotational axes of the rollers are substantially parallel to a central axis of the stent, wherein the rollers are rotated about the central axis of the stent thereby bringing the rollers into contact with the radiopaque marker; and as the rollers continue to rotate while the stent is in gap, allowing the rollers to press the radiopaque marker in a manner that couples the radiopaque marker to the stent.

8. The method of claim 7, wherein the stent is supported by the mandrel while the radiopaque marker is pressed with the rollers.

9. The method of claim 7, wherein the stent is prevented from rotating about its central axis.

10. The method of claim 7, wherein each roller rotates about a retaining pin at a center of each roller.

11. The method of claim 7, wherein the radiopaque marker is deformed when it is pressed into a recess formed in a strut of the stent.

12. The method of claim 7, wherein the stent is oriented such that the radiopaque marker avoids contact with the rollers when the stent is first placed in the gap.

13. The method of claim 1, wherein the gap is greater in size than an outer diameter of the stent.

14. The method of claim 1, wherein the first roller rotates about the rotational axis of the first roller, the second roller rotates about the rotational axis of the second roller, and the rotation of the first roller about the rotational axis of the first roller is in the same direction as the rotation of the second roller about the rotational axis of the second roller.

15. The method of claim 1, further comprising expanding a portion of the marker in the recess.

16. The method of claim 1, further comprising passing the stent through the gap between the first and second rollers, wherein the first and second rollers move apart when the stent passes through the gap.

17. The method of claim 7, wherein the gap is greater than or equal to an outer diameter of the stent.

18. The method of claim 7, further comprising expanding a portion of the marker in a recess formed in a strut of the stent.

19. The method of claim 7, wherein placing the stent in the gap between the first and second rollers includes passing the stent through the gap, wherein the first and second rollers move apart when the stent passes through the gap.

* * * * *